United States Patent
Svenningsson et al.

(10) Patent No.: US 8,470,548 B2
(45) Date of Patent: Jun. 25, 2013

(54) DIAGNOSIS OF DEPRESSION

(75) Inventors: Per Svenningsson, New York, NY (US); Paul Greengard, New York, NY (US)

(73) Assignee: Intra-Cellular Therapies, Inc., New York ( * ) Notice: Subject to any disclaimer, the term of this patent is extended or adjusted under 35 U.S.C. 154(b) by 0 days.

(21) Appl. No.: 13/335,402

(22) Filed: Dec. 22, 2011

(65) Prior Publication Data
US 2012/0178797 A1 Jul. 12, 2012

Related U.S. Application Data

(63) Continuation of application No. 12/308,352, filed as application No. PCT/US2007/013948 on Jun. 13, 2007, now abandoned.

(60) Provisional application No. 60/813,170, filed on Jun. 13, 2006, provisional application No. 60/878,730, filed on Jan. 5, 2007.

(51) Int. Cl.
| G01N 33/53 | (2006.01) |
| G01N 33/567 | (2006.01) |
| G01N 33/542 | (2006.01) |
| C12Q 1/68 | (2006.01) |

(52) U.S. Cl.
USPC ............... 435/7.92; 436/501; 436/504

(58) Field of Classification Search
None
See application file for complete search history.

(56) References Cited

U.S. PATENT DOCUMENTS
2004/0142897 A1 7/2004 Waisman et al.

FOREIGN PATENT DOCUMENTS
WO WO 99/32619 7/1999

OTHER PUBLICATIONS
Donato, R., et al., *Biochim. Biophys. Acta*, vol. 1450, p. 191, (1999).
Sharp, T., "A New Molecule to Brighten the Mood," Science, vol. 311, pp. 45-46, (2006).
Su, T.P., et al., *Journal of Pyschiatric Research*, vol. 43, pp. 1078-1085, (2009).
Svenningsson, et al., Alterations in 5-HT1B Receptor Function by p11 in Depression-Like States; Science 311, pp. 77-80, (2006).
Svenningsson, et al., p11 (S100A10)—An Inducible Adaptor Protein that Modulates Neuronal Functions; Current Opinion in Pharmacology 7, pp. 27-32, (2007).
Ursano, R.J., *Brain Research*, vol. 1293, pp. 2-12, (2009).
Warner-Schmidt, J., et al., "Role of P11 in Cellular and Behavioral Effects of 5HT4 Receptor Stimulation", J. Neurosci., vol. 29, No. 6, pp. 1937-1946, (2009).
Zhang, X., et al., "Evidence for a Role of the 5HT Receptor and Its Adaptor Protein, p11, in L-DOPA Treatment of an Animal Model of Parkisonism," Proc. Natl. Acad. Sci. U.S.A. vol. 105, No. 6, pp. 2163-2168, (2008).

*Primary Examiner* — Olga N Chernyshev
(74) *Attorney, Agent, or Firm* — Hoxie & Associates, LLC

(57) ABSTRACT

The present invention relates to the use of p11 as a drug target as well as a tool for the diagnosis, treatment and development of p11/5-HT receptor related disorders. The invention further relates to p11 knock-out animals as well as p11 transgenic animals and their use as models for the development of novel psychotherapeutic agents, and to methods of diagnosis, prophylaxis and treatment of p11/5-HT receptor related disorders.

9 Claims, No Drawings

```
                         SEQUENCE LISTING

<160> NUMBER OF SEQ ID NOS: 10

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
cgcgtttgga atcactacag ggatg                                          25

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
gaaattgaga tggtgcacga tgcac                                          25

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ggcttaccca tacgatgttc                                                20

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
tatagtcgac atgatgccat cccaaatgg                                      29

<210> SEQ ID NO 5
<211> LENGTH: 61
<212> TYPE: DNA
<213> ORGANISM: Artificial Sequence
<220> FEATURE:
<223> OTHER INFORMATION: Primer

<400> SEQUENCE: 5
tataaagctt ctacaaatct tcttcagaaa tcaattttg ttcagatttc ttcccctttct    60 g                                                                    61
```

-continued

```
<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
gagctgctta atgaggtcgg aatc                                          24

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
tctaaagggc aaaagtgagt atgg                                          24

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
cattcagagg tgaaccctgc tgaggg                                        26

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
cctgtcagcc actctatatg ctcctaatc                                     29

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
ggccagctca ttcctcccac tcatg                                         25
```

DIAGNOSIS OF DEPRESSION

CROSS REFERENCE TO RELATED APPLICATIONS

This application is a continuation of U.S. patent application Ser. No. 12/308,352, filed Dec. 12, 2008 now abandoned, which is a 35 U.S.C. §371 National Phase Application of International Application No. PCT/US2007/013948 filed Jun. 13, 2007, which claims the benefit of U.S. Provisional Applications 60/813,170 filed Jun. 13, 2006 and 60/878,730 filed Jan. 5, 2007, the contents of each of which are herein incorporated by reference in their entirety.

TECHNICAL FIELD

The present invention introduces a biological association between p11 and 5-$HT_{1B}$ and 5-$HT_4$ receptors, providing the use of p11 as a drug target for diseases involving these receptors, as well as a diagnostic tool for the identification of patients suffering from p11/5-HT receptor related disorders.

BACKGROUND OF THE INVENTION

Currently available anti-depressant and anti-anxiety drugs target the bio-synthetic, degradative and operative pathways of monoamine neurotransmitters such as norepinephrine, dompamine and, in particular, serotonin (5-hydroxytryptamine or 5-HT). Serotonin, first discovered in the late 1940's, plays a crucial role in modulating numerous functions in the body including mood, sleep, appetite and sexual activities. It functions both as a neurotransmitter within the central nervous system and also as a peripheral signal modulator. Consequently, alterations in serotonin availability and activity have been linked to depression, eating disorder (e.g. bulimia), obsessive compulsive disorders (OCD), drug addiction, attention deficit disorder (ADD), attention deficit hyperactive disorder (ADHD), premenstrual syndrome, anxiety disorders, aggression, sleep disorders, sexual dysfunction, gastrointestinal disorders (e.g. irritable bowel syndrome), mania, migrane, and bipolar disorder. Conventional anti-depressants typically regulate the signal transmission by either (1) preventing the degradation of serotonin by inhibiting monoamine oxygenase or (2) increasing neuronal transport of serotonin by inhibiting serotonin re-uptake by the presynaptic neurons. Despite over half a century of intensive study of serotonin pathways, however, the understanding of these pathways is incomplete, and there are no established biochemically-based diagnostics or biomarkers for serotonin pathway dysfunction.

5-HT (serotonin) receptors are heterogeneous and are found on the surface of a variety of cells. The 5-$HT_{1B}$ receptor is one of 14 serotonin receptor subtypes and is found abundantly throughout the central nervous system. The structure, distribution and apparent function of 5-$HT_{1B}$ receptors are very similar in rodents and humans. This receptor has been linked to a diverse range of physiologic functions and behaviors including mood, cognition, aggression, addiction, sleep and feeding. 5-$HT_{1B}$ receptors are found both on serotonin- and nonserotonin-containing neurons. 5-$HT_{1B}$ receptors are found predominantly on the pre-synaptic portion of the neuron, where they function as terminal autoreceptors involved in the regulation of serotonin release by neurons. When stimulated by binding to serotonin, they inhibit the release of additional serotonin by the neuron; when not stimulated, serotonin release is enhanced. Blocking of these 5-$HT_{1B}$ receptors thus tends to enhance serotonin levels. There is some evidence that 5-$HT_{1B}$ receptors are heteroreceptors, involved in controlling the release of other neurotransmitters, such as acetylcholine, glutamate, dopamine, norepinepherine and gamma-aminobutyric acid, as well as serotonin. Some 5-$HT_{1B}$ receptors are also found post-synaptically. The 5-$HT_4$ receptor is found in the gastrointestinal system, where it is involved in gastrointestinal motility, as well as the central nervous system. Whereas 5-$HT_{1B}$ is generally associated with a decrease in cAMP, the 5-$HT_4$ receptor is associated with increased cAMP activity. 5-$HT_4$ receptors in the brain modulate neurotransmitter (acetylcholine, dopamine, serotonin and GABA) release and enhance synaptic transmission. They may also play a role in memory enhancement, by promoting release of non-amyloidogenic soluble amyloid precursor protein (sAPPalpha). As Alzheimer's disease is widely thought to be mediated by deposition of beta-amyloid plaque formation, enhancing 5-$HT_4$ receptor function, thereby enhancing release of sAPPalpha, represents a potential approach to treatment or prophylaxis of Alzheimer's disease.

The protein p11 is a member of the S100 EF-hand protein family. p11 is also known as annexin-II light chain, lipocortin-II light chain, calpactin I light chain, 42C, or S-100 related protein, and these terms may be used interchangeably herein. R. Donato, *Biochim. Biophys. Acta,* 1450, 191 (1999). It is present in a variety of cells separately or as a heterotetramer. The heterotetramer is composed of two copies of p36, also known as armexin-II or calpactin-I heavy chain, and two copies of p11. Within the cell, the heterotetramer is localized at the cytoplasmic surface of the plasma membrane in the submembranous cytoskeleton, and it is suggested that the complex may play a role in membrane trafficking events such as exocytosis, endocytosis and cell-cell adhesion. p11 has been claimed to have a role in tumor cell invasion, tumor growth, and metastasis. US 2004/0142897A1. p11 has not previously been identified as being involved with 5-HT receptors or psychiatric disorders.

SUMMARY OF THE INVENTION

Applicants have now surprisingly discovered that p11 protein interacts specifically with 5-$HT_{1B}$ receptors and appears to help regulate signaling of the brain messenger chemical serotonin, a key target of many psychotherapeutic agents. Svenningsson et al., *Science* (2006) 331:77-80; Svenningsson et al., *Current Opinion in Pharmacology* (2006), 6:1-6 (both incorporated herein by reference). p11 appears to play a crucial role in the recruitment of 5-$HT_{1B}$ receptors to the neuronal plasma membrane where they are more functional. Applicants have further discovered that p11 also interacts with 5-$HT_4$ receptors. Applicants have shown that p11 levels may be directly involved in the development of depression, anxiety disorders and similar psychiatric illnesses that are thought to involve faulty serotonin receptors. Comparison of p11 levels in the brains of depressed subjects (depressed humans and mice models) to those of non-depressed subjects (non-depressed humans and control mice) shows a substantially lower level of p11 in depressed subjects compared to non-depressed subjects. Moreover, p11 levels tend to be higher in subjects treated with various types of antidepressants, including tricyclic antidepressants, monoamine oxidase inhibitors (MAOIs) and electroconvulsive therapy. There is an over-expression of p11 in animals that are treated with anti-depressants. For example, we have observed that monkeys receiving the selective serotonin reuptake inhibitor fluoxetine display a significant (more than twofold) increase in p11 expression in peripheral blood mononuclear cells (PBMC), and similar effects are demonstrated in the brains of mice receiving fluoxetine. Similarly, animal models with a p11 knock-out gene exhibit fewer $5\text{-HT}_{1B}$ receptors at the neuronal plasma membrane, have reduced serotonin signaling, and exhibit a depression-like phenotype. Interestingly, p11 expression decreases in response to excess levels of glucocorticoid hormones, which are often released in response to stress, which in light of Applicants' work, provides a possible biochemical explanation for the observed link between depression and highly stressful events. Based on these surprising discoveries by Applicants, p11 is shown to be a suitable diagnostic target as well as a drug target and screening tool for the development of treatments for disorders previously associated with $5\text{-HT}_{1B}$ or $5\text{-HT}_4$ receptors, or with serotonin function (or lack thereof).

The term "p11/5-HT receptor related disorders" as used herein include any disorders mediated by, associated with, caused by, affected by, triggered by or involving mobilization (or lack of mobilization) of 5-HT receptors, e.g., $5\text{-HT}_{1B}$ or $5\text{-HT}_4$ receptors, by the p11 protein. p11/5-HT receptor related disorders may include, but are not limited to, psychiatric disorders (e.g. depression, anxiety disorders, aggression, mania, bipolar disorder, attention deficit disorder, attention deficit hyperactive disorder, drug addiction and obsessive compulsive disorder, and Alzheimer's disease) sleep disorders (e.g. insomnia), eating disorders (e.g. bulimia), sexual dysfunction, and gastrointestinal disorders (e.g. irritable bowel syndrome); especially depression.

The invention thus provides, inter alia:
1. Methods of diagnosing p11/5-HT receptor related disorders;
2. Methods of identifying compounds useful in treating p11/5-HT receptor related disorders;
3. Transgenic animals which over- or under-express p11; and
4. Methods of treating p11/5-HT receptor related disorders.

DETAILED DESCRIPTION OF THE INVENTION

In one embodiment, the invention relates to a method of diagnosing p11/5-HT receptor related disorders in a subject comprising (1) assaying the level of p11 protein in a biological sample of said subject, e.g., a blood or tissue sample, for example monocytes and/or leukocytes, e.g., peripheral blood mononuclear cells (PBMC), and (2) comparing said p11 level to a reference standard, e.g., the p11 level in a control population that does not have or is not suspected of having any p11/5-HT receptor related disorders, wherein an abnormal level of p11 in a subject compared to the reference standard constitutes a positive diagnosis of p11/5-HT receptor related disorders (Method 1).

Thus the invention includes the following embodiments of Method 1

1.1. The method of Method 1 wherein the p11/5-HT receptor related disorder is a disorder associated with an abnormally low level of p11, wherein a reduced level of p11 in a subject compared to the reference standard constitutes a positive diagnosis of such disorders.
1.2. A method according to method 1 or 1.1, wherein the disorder is associated with an abnormally low level of p11 and is selected from a group consisting of depression, obsessive compulsive disorder, drug addiction, eating disorders, attention deficit disorder and attention deficit hyperactive disorder.
1.3. A method according to any of the previous methods wherein the disorder is associated with an abnormally low level of p11 and is depression.
1.4. A method according to method 1 wherein said p11/5-HT receptor related disorders are disorders associated with an abnormally high level of p11, wherein an elevated level of p11 in a subject compared to that of the reference standard constitutes a positive diagnosis of such disorders.
1.5. A method according to any of method 1 or 1.4 wherein the disorder is associated with an abnormally high level of p11 and is selected from a group consisting of mania, bipolar disorder, anxiety disorders, aggression, sleep disorders, sexual dysfunction and gastrointestinal disorders.
1.6. The method according to any of the foregoing methods wherein said level of p11 is determined by assaying p11 protein level in peripheral blood mononuclear cells (PBMC) from said subject.
1.7. The method according to 1.6 wherein the PBMCs are selected from monocytes, NK cells, and CD-8+ T-cells.
1.8. The method according to any of the foregoing methods, wherein said level of p11 is determined by assaying p11 mRNA level in a biological sample from said subject.
1.9. The method according to any of the foregoing methods wherein the level of p11 is determined using a monoclonal antibody specific for p11.
1.10. The method according to any of the foregoing methods wherein the p11/5-HT receptor related disorder is a p11/5-$\text{HT}_{1B}$ receptor related disorder.
1.11. The method according to any of the foregoing methods wherein the p11/5-HT receptor related disorder is a p11/5-$\text{HT}_4$ receptor related disorder.
1.12. A kit useful in measuring p11 levels, e.g. in accordance with any of the foregoing methods 1-1.11, comprising an oligonucleotide probe specific for p11 mRNA or a monoclonal antibody specific for p11, and instructions for use.
1.13. Use of an oligonucleotide probe specific for p11 mRNA or a monoclonal antibody specific for p11 in any of methods 1-1.11.
1.14. Use of an oligonucleotide probe specific for p11 mRNA or a monoclonal antibody specific for p11 in the manufacture of a reagent for use in a method according to any of claims 1-1.11 or in a kit according to 1.12.

In another embodiment, the invention relates to a method to identify p11 modulators useful to treat or ameliorate p11/5-HT receptor related disorders comprising assaying for the ability of a candidate modulator to regulate (either up or down) p11 expression or p11 activities associated with 5-HT receptors (method 2).

Therefore, method 2 includes
2.1. A method to identify p11 modulators useful to treat or ameliorate p11/5-HT receptor related disorders comprises the steps of providing a first sample and a second sample, e.g., a cell culture or cell or tissue sample, containing equivalent amounts of p11 gene product (e.g., protein or mRNA); contacting the first sample with the candidate p11 modulator; and determining whether the amounts of p11 gene product in the first sample has changed, wherein an increased amount of gene product indicate that the candidate modulators can be useful to treat or ameliorate disorders associated with abnormally low level of p11 while a decreased amount indicates that the candidate modulators can be useful to treat or ameliorate disorders associated with abnormally low level of p11.
2.2. A method to identify p11 modulators useful to treat or ameliorate p11/5-HT receptor related disorders comprises the steps of providing a first sample and a second sample containing equivalent number of $5\text{-HT}_{1B}$ and/or $5\text{-HT}_4$ receptors at cell surface; contacting the first sample with the candidate p11 modulator; and determining whether the number of $5\text{-HT}_{1B}$ and/or $5\text{-HT}_4$ receptors at cell surface of the first sample has changed relative to the second sample, wherein an increased number of 5-$HT_{1B}$ and/or 5-$HT_4$ receptors at cell surface indicate that the candidate modulators can be useful to treat or ameliorate disorders associated with abnormally low level of p11 while a decreased number of 5-$HT_{1B}$ and/or 5-$HT_4$ receptors at cell surface indicates that the candidate modulators can be useful to treat or ameliorate disorders associated with abnormally low level of p11.

2.3. A method to identify p11 modulators comprising contacting a candidate p11 modulator with a cell comprising a reporter gene operably linked to a p11 promoter, and using the reporter gene expression level as a proxy for p11 expression.

2.4. A method to identify p11 modulators useful to treat or ameliorate disorders associated with low levels of p11, comprising assaying for the ability of a candidate modulator to up-regulate p11 expression or increase p11 activities associated with 5-$HT_{1B}$ and/or 5-$HT_4$ so as to recruit 5-$HT_{1B}$ and/or 5-$HT_4$ receptors at the neuronal plasma membrane.

2.5. A method according to any of methods 2-2.4 wherein the disorders associated with abnormally low levels of p11 are selected from depression, obsessive compulsive disorder, drug addiction, eating disorders, attention deficit disorder or attention deficit hyperactive disorder, and Alzheimer's disease.

2.6. A method according to any of the preceding methods 2-2.5 wherein the disorder is depression.

2.7. A method according to any of the preceding methods 2-2.6 wherein a modulator of p11 is used as a positive control.

2.8. A method according to method 2.6 wherein the modulator of p11 is selected from tricyclic antidepressants, selective serotonin reuptake inhibitors, triptans, and monoamine oxidase inhibitors.

2.9. A method according to method 2.8 wherein the modulator of p11 is a tricyclic antidepressant selected from amitriptyline (brand name: Elavil), desipramine (brand name: Norpramin), imipramine (brand name: Tofranil), and nortriptyline (brand name: Aventyl, Pamelor)

2.10. A method according to method 2.8 wherein the modulator of p11 is imipramine.

2.11. A method according to method 2.8 wherein the modulator of p11 is a Monoamine Oxidase Inhibitors (MAOI), e.g., selected from isocarboxazid (brand name: Marplan); phenelzine (brand name: Nardil) and tranlcypromine (brand name: Parnate)

2.12. A method according to 2.11 wherein the MAOI is tranicypromine.

2.13. A method according to method 2.8 wherein the modulator of p11 is a selective serotonin reuptake inhibitor, e.g., selected from citalopram (brand name: Celexa); escitalopram (brand name: Lexapro); fluoxetine (brand name: Prozac); paroxetine (brand names: Paxil, Pexeva); sertraline (brand name: Zoloft).

2.14. A method to identify p11 modulators useful to treat or ameliorate disorders associated with high levels of p11, comprising assaying for the ability of a candidate modulator to down-regulate p11 expression or inhibit or reduce p11 activities associated with 5-$HT_{1B}$ and/or 5-$HT_4$ so as to reduce or inhibit p11's ability to recruit 5-$HT_{1B}$ and/or 5-$HT_4$ receptors to neuronal plasma membrane.

2.15. A method according to 2.14 wherein the disorders associated with high levels of p11 include, but are not limited to mania, dipolar disorder, anxiety disorders, aggression, sleep disorders, sexual dysfunction and gastrointestinal disorders.

2.16. A method according to 2.15 to identify p11 modulators useful to treat or ameliorate disorders associated with high levels of p11, wherein said modulators are selected from siRNA, antisense oligonucleotides, and monoclonal antibodies to p11.

2.17. A method according to any of methods 2-2.16 wherein p11 suppressor compounds selected from siRNA, antisense oligonucleotides, and monoclonal antibodies to p11 are used as controls or comparators.

2.18. A method e.g. according to any of method 2-2.17 to identify p11 mimetics useful to treat or ameliorate disorders associated with abnormally low level of p11, comprising assaying for the ability of a candidate p11 mimetic to associate or interact with 5-$HT_{1B}$ and/or 5-$HT_4$ receptors so as to recruit 5-$HT_{1B}$ and/or 5-HT4 receptors to the neuronal plasma membrane.

2.19. A method according to method 2.18 to identify p11 mimetics useful to treat or ameliorate depression comprising assaying for the ability of a candidate p11 mimetic to recruit 5-$HT_{1B}$ and/or 5-$HT_4$ receptors to the neuronal plasma membrane.

2.20. The method according to any of the foregoing methods wherein the p11/5-HT receptor related disorder is a p11/5-$HT_{1B}$ receptor related disorder.

2.21. The method according to any of the foregoing methods wherein the p11/5-HT receptor related disorder is a p11/5-$HT_4$ receptor related disorder.

2.22. A cell comprising a reporter gene operably linked to a p11 promoter.

2.23. Use of a cell according to 2.22 in a method according to any of methods 2-2.21.

In yet another embodiment, the invention is directed to a transgenic non-human mammal or progeny thereof, which over- or underexpresses p11, and their use in methods to discover new pharmaceuticals (method 3). The invention thus includes 3.1. A p11 knock-out non-human mammal, wherein said non-human mammal possesses a DNA sequence that has a defect, mutation or deficiency in the p11 gene and therefore under-expresses p11 proteins and/or possesses fewer 5-$HT_{1B}$ and/or 5-HT4 receptors at the neuronal plasma membrane and therefore exhibits a depression-like phenotype compared to a wild-type nonhuman mammal of the same species.

3.2. A p11 transgenic non-human mammal, wherein said non-human mammal overexpresses p11 proteins and/or exhibits an elevated level of 5-$HT_{1B}$ and/or 5-$HT_4$ receptors at the neuronal plasma membrane and therefore exhibits a hyperactive phenotype compared to a wild-type non-human mammal of the same species.

3.3. A non-human mammal according to 3.1 or 3.2 which is a mouse.

3.4. A non-human mammal, e.g. according to 3.2 or 3.3, having a transgene comprising a coding region encoding p11, operably linked to a regulatable promoter, e.g. the doxycycline-regulatable calcium/calmodulin-dependent protein kinase II (CamKII) promoter.

3.5. A method to study p11/5-HT receptor related disorders or to develop novel psychotherapeutic agents useful to treat or ameliorate p11/5-HT receptor related disorders comprising (1) administering said agents to (a) p11 knock-out mammals according 3.1 or 3.3 and (b) control mammals of the same species that do not have or are not suspected of having any p11/5-HT receptor related disorders; and (2)

assessing and comparing the behavior and/or levels of 5-HT$_{1B}$ or 5-HT$_4$ receptor of said (a) knock-out mammals and (b) control mammals.

3.6. A method, e.g. according to 3.4, to study depression comprising administering an antidepressant to (a) p11 knock-out mammals and (b) control mammals that do not have or is not suspected of having depression; and (2) assessing and comparing the behavior and/or 5-HT$_{1B}$ or 5-HT$_4$ receptor levels of said (a) knock-out mammals and (b) control mammals.

3.7. A p11 mouse model useful for developing novel antipsychotic agents comprising (1) administering said agents to (a) p11 over-expressing mice and (b) control mice that do not have or is not suspected of having any p11/5-HT receptor related disorders; and (2) assessing and comparing the p11 levels of said (a) transgenic mice and (b) control mice.

3.8. A method to study p11/5-HT receptor related disorders or to develop novel psychotherapeutic agents useful to treat or ameliorate p11/5-HT receptor related disorders comprising (1) administering said agents to (a) mammals according 3.2 or 3.3 and (b) control mammals of the same species that do not have or are not suspected of having any p11/5-HT receptor related disorders; and (2) assessing and comparing the p11 levels of said (a) mammals according to 3.2 or 3.3 and (b) control mammals.

3.9. A p11 mouse model useful for developing novel antipsychotic agents comprising (1) administering said agents to (a) p11 over-expressed mice, e.g. according to 3.2 and (b) control mice that do not have or is not suspected of having any p11/5-HT receptor related disorders; and (2) assessing and comparing the behavior and/or p11 or 5-HT receptor levels of said (a) transgenic mice and (b) control mice.

3.10. The method or model according to any of the foregoing methods or models wherein the 5-HT receptor being measured or being over- or under-expressed is the 5-HT$_{1B}$ receptor.

3.11. The method or model according to any of the foregoing methods or models wherein the 5-HT receptor being measured or being over- or under-expressed is the 5-HT$_4$ receptor.

The invention further relates to a method to treat a patient suffering from a p11/5-HT receptor related disorder, comprising administration of a therapeutically effective amount of a p11 modulator (method 4).

4.1. Method 4 when the patient is first identified according to any of methods 1-1.11.

4.2. Method according to 4 or 4.1 wherein the p11/5-HT receptor related disorder is a disorder associated with abnormally low levels of p11, e.g., selected from depression, obsessive compulsive disorder, drug addiction, eating disorders, attention deficit disorder or attention deficit hyperactive disorder, and Alzheimer's disease.

4.3. Method according to 4.2 wherein the disorder is depression.

4.4. Method according to any of the previous methods 4-4.3 comprising administration of a p11 modulator identified in accordance with method 3, e.g. using any of embodiments 3.1-3.11.

4.5. A method according to any of the previous methods wherein the modulator of p11 is selected from tricyclic antidepressants, selective serotonin reuptake inhibitors, and monoamine oxisdase inhibitors.

4.6. A method according to method 4.4 wherein the modulator of p11 is a tricyclic antidepressant selected from amitriptyline (brand name: Elavil), desipramine (brand name: Norpramin), imipramine (brand name: Tofranil), and nortriptyline (brand name: Aventyl, Pamelor)

4.7. A method according to method 4.5 wherein the modulator of p11 is imipramine.

4.8. A method according to method 4.4 wherein the modulator of p11 is a Monoamine Oxidase Inhibitors (MAOI) selected from isocarboxazid (brand name: Marplan); phenelzine (brand name: Nardil) and tranlcypromine (brand name: Parnate)

4.9. A method according to 4.8 wherein the MAOI is tranlcypromine.

4.10. A method according to method 4.4 wherein the modulator of p11 is a selective serotonin reuptake inhibitor selected from citalopram (brand name: Celexa); escitalopram (brand name: Lexapro); fluoxetine (brand name: Prozac); paroxetine (brand names: Paxil, Pexeva); sertraline (brand name: Zoloft).

4.11. A method according to any of the previous methods 4-4.10 to treat or ameliorate in a subject suffering from p11/5-HT receptor related disorders comprising administering to said subject an effective amount of p11 modulator or mimetic so as to regulate (up or down) p11 expression and/or 5-HT$_{1B}$ or 5-HT$_4$ receptors at the neuronal plasma membrane.

4.12. A method according to 4.11 treat or ameliorate in a subject suffering from disorders associated with abnormally low level of p11 comprising administering to said subject an effective amount of p11 modulator or mimetic so as to up-regulate p11 expression or recruit 5-HT$_{1B}$ or 5-HT$_4$ receptors to the neuronal plasma membrane.

4.13. A method according to 4.12 wherein the disorder is selected from depression, obsessive compulsive disorder, drug addiction, eating disorders, attention deficit disorder or attention deficit hyperactive disorder, and Alzheimer's disease.

4.14. The method according to any of the foregoing methods wherein the p11/5-HT receptor related disorder is a p11/5-HT$_{1B}$ receptor related disorder.

4.15. The method according to any of the foregoing methods wherein the p11/5-HT receptor related disorder is a p11/5-HT$_4$ receptor related disorder.

4.16. The use of a p11 modulator, e.g., as herein described, in the manufacture of a medicament to treat a p11/5-HT receptor mediated disorder, e.g., in any of methods 4-4.15.

4.17. A pharmaceutical composition comprising a p11 modulator for use in treating a p11/5-HT receptor mediated disorder, e.g., in any of methods 4-4.15.

In another embodiment, the invention relates to a method to enhance p11 expression or upregulate p11 in a patient suffering from a p11/5-HT receptor related disorder, comprising the administration of a nucleic acid expressing p11 or inducing the expression of p11 in the brain of said patient, wherein said nucleic acid up-regulates p11 or increases p11 expression in the brain of said patient (Method 5). The nucleic acid encoding or inducing the expression of p11 is preferably delivered to the brain of the patient by a vector or by cells comprising the nucleic acid. Such vectors may be in the form of DNA or RNA in a suitable delivery system, for example liposome-encapsulated DNA constructs or in the form of a viral vector, for example a replication deficient adenoviral vector or adeno-associated viral vector. In a preferred embodiment, the vector is a viral vector which provides transient expression of the desired transgene rather than integration of the transgene into the infected cell, for example a vector derived from adenovirus. The vector may for example comprise DNA encoding p11 operably linked to a promoter, e.g., a constitutive promoter (e.g., such as the CMV promoter), a tissue-specific promoter (e.g., such as the neuron-specific enolase (NSE) promoter) or an inducible promoter (e.g., a tetracycline or doxycycline inducible promoter), that controls the expression of the DNA encoding p11 so as to enable the expression of p11 in the target cell. For example, a viral vector may be a recombinantly modified adenovirus comprising a p11 DNA construct under control of a tissue-specific promoter and lacking a functional copy of one or more genes essential for replication (for example, the E1 and/or E3 gene), such that the virus can replicate only in a helper cell line or other environment where the product of the gene or genes essential for replication is supplied. Viral vectors may also comprise surface modifications to reduce immunogenicity and/or to target the vectors to the desired cells. Viral vectors suitable for gene therapy in the CNS are known in the art, e.g., including vectors targeted to CNS cells and vectors utilizing tissue specific or inducible promoters for expression of the transgene, for example as described in Benitez, et al., "Gene Therapy Targeting in Central Nervous System", *Current Gene Therapy* (2003) 3: 127-145 (incorporated herein by reference). Non-viral nucleic acid delivery systems may comprise nucleic acid associated or complexed with agents to facilitate the entry of the nucleic acid across the cellular membrane. Examples of such non-viral vector complexes include the formulation with polycationic agents which facilitate the condensation of the DNA and lipid-based delivery systems, for example a liposome based delivery system. In another embodiment, said nucleic acid expressing or inducing the expression of p11 is delivered by a cell, for example a neuronal stem cell which expresses p11 at levels higher than the levels expressed by the patient's cells, which is transplanted into the brain of the patient. The source of the cell may be the patient or a human donor. The p11 expression in the transplanted cell may be achieved by selection for p11 expression and/or by transformation, e.g., ex vivo transformation, with (i) a p11 construct, (ii) a promoter upstream of the native p11 sequence which enhances p11 expression, or (iii) a construct encoding a protein which enhances p11 expression. The cell is preferably stably transformed, e.g., using a retroviral or lentiviral vector, so that the construct is integrated into the genome of the cell. The cellular or viral vectors may further comprise a "safety gene" for example the herpes simplex virus thymidine kinase gene (HSV-tk) which makes a host cell susceptible to gancyclovir, so that the cells or viruses can be easily destroyed if the cells become cancerous or the virus infects the patient or there is otherwise a risk of harm to the patient. In a preferred embodiment, the nucleic acid enhancing p11 expression (for example a cell or viral vector comprising a construct expressing p11) is introduced into the targeted cell via intracerebral administration, e.g., into the hippocampus region. The nucleic acid may be administered in a single dose or a multiplicity of treatments.

Therefore, the invention further provides methods as follows:

5.1 Method 5, wherein said method increases p11 expression.
5.2 Method 5 or 5.1, wherein the nucleic acid construct is capable of expressing p11 in a brain cell.
5.3 Method 5, 5.1-5.2, wherein the p11/5-HT receptor related disorder is a disorder associated with abnormally low levels of p11, e.g., selected from depression, obsessive compulsive disorder, drug addiction, eating disorders, attention deficit disorder or attention deficit hyperactive disorder, and Alzheimer's disease.
5.4 Method 5, 5.1-5.2, wherein the p11/5-HT receptor related disorder is anxiety disorder or depression.
5.5 Method 5, 5.1-5.2 wherein the p11/5-HT receptor related disorder is depression.
5.6 Method 5, 5.1 or 5.5, wherein said nucleic acid encoding p11 is delivered by a replication-deficient adenoviral vector comprising DNA encoding p11.
5.7 Method 5.6, wherein the DNA encoding p11 is under control of a tissue specific promoter, for example the NSE promoter.
5.8 Method 5, 5.1 or 5.5, wherein said nucleic acid encoding p11 is delivered by a stem cell transformed with a p11 construct.
5.9 Any of Methods 5 or 5.1-5.8, wherein said nucleic acid of p11 is introduced via intracerebral administration.
5.10 Any of methods 5 or 5.1-5.8, wherein said nucleic acid of p11 is introduced to the hippocampus.

As used herein and in the appended claims, the singular forms "a", "an", and "the" include plural reference unless the context clearly dictates otherwise. Thus, for example, reference to the "antibody" is a reference to one or more antibodies and equivalents thereof known to those skilled in the art, and so forth. Treatment of "a" p11/5-HT$_{1B}$ receptor mediated disorder may include treatment of multiple such disorders.

The term "p11" herein refers to any and all forms of p11 polypeptide, including but not limited to, partial forms, isoforms, precursor forms, full length polypeptide, fusion proteins containing the p11 sequence or fragments of any of the above, from human or any other species.

The phrase "p11/5-HT receptor related disorders" herein refers to any disorders mediated by, associated with, caused by, affected by, triggered by or involving p11 protein and its mobilization of 5-HT receptors, especially the 5-HT$_{1B}$ or 5-HT$_4$ receptors. p11/5-HT receptor related disorders may include, but are not limited to, psychiatric disorders (e.g. depression, anxiety disorders, aggression, mania, bipolar disorder, attention deficit disorder, attention deficit hyperactive disorder, Alzheimer's disease, drug addiction and obsessive compulsive disorder) sleep disorders (e.g. insomnia), eating disorders (e.g. bulimia), sexual dysfunction, and gastrointestinal disorders (e.g. irritable bowel syndrome). "Disorders associated with abnormally low level of p11" herein refers to disorders such as depression, obsessive compulsive disorders, drug addiction, eating disorders, attention deficit disorder or attention deficit hyperactive disorder, or Alzheimer's disease, especially depression. Likewise, "disorders associated with abnormally high level of p11" refers to disorders such as mania, dipolar disorder, anxiety disorders, aggression, sleep disorders, sexual dysfunction and gastrointestinal disorders.

The phrase "p11 modulator" refers to any substance or compound (e.g. small molecules or polypeptides as described herein) or methods of treatment (e.g., electroconvulsive therapy) capable of changing (either increasing or decreasing) expression of a gene encoding p11 protein, transcription of a p11 gene or cDNA into an mRNA, the translation of a p11 mRNA into protein, post-translational modification of a p11 protein, cellular or extracellular localization of a p11 protein, or amount of p11 localized in or on the cell membrane or inside the cell, relative to the p11 activity in similar cells. The term "p11 modulator" also refers to any substance capable of affecting (either positively or negatively) the ability of p11 proteins to recruit 5-HT$_{1B}$ receptors to the neuronal plasma membrane. Examples of p11 modulators useful to treat disorders associated abnormally low level of p11 such as depression include tricyclic antidepressants (e.g. imipramine (Tofranil®), amitriptyline (ELAVIL®, ENDEP® TRYPTANOL®), clomipramine (ANAFRANIL®), desipramine (NORPRAMIN®, PERTOFRANE®), lofepramine (GAMANIL®, LOMONT®), nortriptyline (PAMELOR®), trimipramine (SURMONTIL®)). Other modulators useful to treat or ameliorate disorders associated with low level of p11 (e.g. depression) include Monoamine Oxidase Inhibitors (MAOI) (e.g. Tranylcypromine (Parnate), Isocarboxazid (Marplan), Moclobemide (Aurorix, Manerix, MOCLODURA®) or Phenelzine (Nardil)), and selective serotonin reuptake inhibitors (e.g., citalopram (brand name: Celexa); escitalopram (brand name: Lexapro); fluoxetine (brand name: Prozac); paroxetine (brand names: Paxil, Pexeva); sertraline (brand name: Zoloft)).

Conventional screening assays (both in vitro and in vivo) may be used to identify modulators that inhibit or induce p11 activity and/or p11 gene expression. One such assay is a gene reporter assay, wherein cells transfected with a reporter construct comprising a marker gene (e.g., luciferase or green fluorescent protein (GFP)) downstream of a p11 binding site are contacted with a candidate modulator compound and the changes in the expression of the marker protein is measured and compared to a transfected cell sample that is not contacted with any modulator. Candidate modulators that either inhibit or induce marker protein expression are identified as drugs useful for the treatment of p11/5-HT receptor related disorder. Candidate modulators that inhibit marker protein expression would be useful drug candidates for the treatment of disorders associated with abnormally high level of p11 while a candidate modulators that induce marker protein expression would be useful drug candidates for the treatment of disorders associated with abnormally low level of p11.

p11 modulators may include, e.g., natural or unnatural chemical compounds, in free or pharmaceutically acceptable salt form, sense or antisense p11 oligonucleotides, inhibitory antibodies to p11, p11-receptor blocking peptides, p11 antagonists, si RNA, triple helix DNA, ribozymes, RNA aptamers and/or double stranded RNA. The term "antisense" as used herein, refers to nucleotide sequences which are complementary to a specific DNA or RNA sequence. Therefore, "p11 antisense polynucleotide" refers to any nucleotide sequence that is complementary to p11 DNA or RNA sequence. Functionally, p11 antisense polynucleotide is capable of decreasing the expression of p11 protein in a cell. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines natural sequences produced by the cell to form duplexes. These duplexes then block either the further transcription or translation. The designation "negative" is sometimes used in reference to the antisense strand, and "positive" is sometimes used in reference to the sense strand. Similarly, the term "sense" as used herein, refers to nucleotide sequences which can be translated to produce a specific polypeptide or fragment thereof. Therefore, "p11 sense polynucleotide" refers to any nucleotide sequence that can be translated to produce p11 polypeptide or fragment thereof. Functionally, p11 sense polynucleotide is capable of increasing the expression of p11 proteins in a cell.

Specifically, substances that inhibit the expression of p11 at the nucleic acid level may include ribozymes, antisense oligonucleotides, triple helix DNA, RNA aptamers and/or double stranded RNA directed to an appropriate nucleotide sequence of the p11 nucleic acid. These inhibitory molecules may be created using conventional techniques by one of skill in the art without undue burden or experimentation. For example, modifications (e.g. inhibition) of gene expression can be obtained by designing antisense molecules, DNA or RNA, to the control regions of the genes encoding the polypeptides discussed herein, i.e. to promoters, enhancers, and introns. For example, oligonucleotides derived from the transcription initiation site, e.g., between positions −10 and +10 from the start site may be used. Notwithstanding, all regions of the gene may be used to design an antisense molecule in order to create those which gives strongest hybridization to the mRNA and such suitable antisense oligonucleotides may be produced and identified by standard assay procedures familiar to one of skill in the art.

Similarly, inhibition of the expression of gene expression may be achieved using "triple helix" base-pairing methodology. Gee, J. E. et al. (1994) In: Huber, B. E. and B. I. Carr, *Molecular and Immunologic Approaches*, Futura Publishing Co., Mt. Kisco, N.Y.). These molecules may also be designed to block translation of mRNA by preventing the transcript from binding to ribosomes. Ribozymes, enzymatic RNA molecules, may also be used to inhibit gene expression by catalyzing the specific cleavage of RNA. The mechanism of ribozyme action involves sequence-specific hybridization of the ribozyme molecule to complementary target RNA, followed by endonucleolytic cleavage. Examples which may be used include engineered "hammerhead" or "hairpin" motif ribozyme molecules that can be designed to specifically and efficiently catalyze endonucleolytic cleavage of gene sequences, for example, the gene for p11. Specific ribozyme cleavage sites within any potential RNA target are initially identified by scanning the target molecule for ribozyme cleavage sites which include the following sequences: GUA, GUU and GUC. Once identified, short RNA sequences of between 15 and 20 ribonucleotides corresponding to the region of the target gene containing the cleavage site may be evaluated for secondary structural features which may render the oligonucleotide inoperable. Grassi and Marini, 1996, Annals of Medicine 28: 499-510; Gibson, 1996, Cancer and Metastasis Reviews 15: 287-299; Cotten et al., 1989 EMBO J. 8:3861-3866. RNA aptamers can also be introduced into or expressed in a cell to modify RNA abundance or activity. RNA aptamers are specific RNA ligands for proteins, such as for Tat and Rev RNA (Good et al., 1997, Gene Therapy 4: 45-54) that can specifically inhibit their translation. Gene specific inhibition of gene expression may also be achieved using conventional double stranded RNA technologies. A description of such technology may be found in WO 99/32619 which is hereby incorporated by reference in its entirety.

Antisense molecules, triple helix DNA, RNA aptamers and ribozymes of the present invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding the genes of the polypeptides discussed herein. Such DNA sequences may be incorporated into a wide variety of vectors with suitable RNA polymerase promoters such as T7 or SP6. Alternatively, cDNA constructs that synthesize antisense RNA constitutively or inducibly can be introduced into cell lines, cells, or tissues.

siRNA molecules of the present invention can be generated by annealing two complementary single-stranded RNA molecules together (one of which matches a portion of the target mRNA) (Fire et al., U.S. Pat. No. 6,506,559) or through the use of a single hairpin RNA molecule that folds back on itself to produce the requisite double-stranded portion (Yu et al. (2002) Proc. Natl. Acad. Sci. USA 99:6047-52). The siRNA molecules can be chemically synthesized (Elbashir et al. (2001) Nature 411:494-98) or produced by in vitro transcription using single-stranded DNA templates (Yu et al., supra). Alternatively, the siRNA molecules can be produced biologically, either transiently (Yu et al., supra; Sui et al. (2002) Proc. Natl. Acad. Sci. USA 99:5515-20) or stably (Paddison et al. (2002) Proc. Natl. Acad. Sci. USA 99:1443-48), using an expression vector(s) containing the sense and antisense siRNA sequences. Recently, reduction of levels of target mRNA in primary human cells, in an efficient and sequence-specific manner, is demonstrated using adenoviral vectors that express hairpin RNAs, which are further processed into siRNAs (Arts et al. (2003) Genome Res. 13:2325-32).

As used herein, the phrase "p11 activities" refers to any direct biochemical activity of p11 or indirect activity associated with p11 so as to affect (positively or negatively) p11's interaction with $5\text{-HT}_{1B}$ receptors. Modulators that increase p11 activities with $5\text{-HT}_{1B}$ receptors may be any substance that increases the association of p11 to $5\text{-HT}_{1B}$ receptors so as to increase the ability of p11 proteins to recruit $5\text{-HT}_{1B}$ receptors to the neuronal plasma membrane. Conversely, modulators that inhibit or reduce p11 activities with $5\text{-HT}_{1B}$ receptors may be any substance that blocks or reduces the interaction between p11 and $5\text{-HT}_{1B}$ receptors so as to reduce the ability of p11 proteins to recruit $5\text{-HT}_{1B}$ receptors to the neuronal plasma membrane.

The term "pH mimetic" refers to a natural or unnatural substance or polypeptide or any fragment thereof that mimics p11 protein in structure, function, property and/or activity, thereby modulating, regulating or increasing $5\text{-HT}_{1B}$ receptor availability at the neuronal plasma membrane. p11 mimetic may mimic p11 in whole or in part.

The term "subject" refers to any human or nonhuman organism.

A "control subject" refers to any human or nonhuman organism that does not have and/or is not suspected of having a disorder, syndrome, disease, condition and/or symptom of p11/5-HT receptor related disorders.

The term "biological sample" may include any sample comprising biological material obtained from e.g. an organism, body fluid, waste product, cell or part of a cell thereof, cell line, biopsy, tissue culture or other source containing a p11 protein, polypeptide, oligonucleotide, mRNA or polynucleotide or any fragment of any of the above.

A "positive diagnosis" of a p11/5-HT receptor related disorder refers to a condition where the subject being examined exhibits an abnormal level of p11 compared to control subject who does not have and/or is not suspected of having a p11/5-HT receptor related disorder. Abnormal level refers to a level that is higher or lower than that in a control subject. For instance, a subject with a positive diagnosis of depression exhibits a depressed level of p11 compared to a control subject who does not have and/or is not suspected of having depression and/or symptom thereof. On the other hand, a subject with a positive diagnosis of anxiety disorders state exhibits an elevated p11 expression compared to a control subject who does not have and/or is not suspected of having anxiety disorders and/or symptom thereof.

The level of p11 may be determined by assaying p11 proteins in a sample of tissue or cells obtained from a subject of a type which expresses p11. For example, monocytes and/or lymphocytes may be used. Similarly, p11 level may also be determined by assaying for p11 mRNA level in the sample. p11 gene expression (e.g. mRNA levels) may be determined using methods familiar to one of skill in the art, including, for example, conventional Northern analysis or commercially available micro-arrays. Additionally, the effect of test compounds' inhibition of p11 and/or related regulatory protein levels can be detected with an ELISA antibody-based assay or fluorescent labeling reaction assay. An abnormal level of p11 protein or mRNA in a subject compared to a reference, e.g., a control subject or control population (or a reference standard based on prior measurements in a control population) constitutes a positive diagnosis of p11/5-HT receptor related disorders. Therefore, an elevated level of p11 in a subject compared to the reference constitutes a positive diagnosis of disorders associated with high levels of p11, e.g. mania, dipolar disorder, anxiety disorders, aggressive disorder, sleep disorders, sexual dysfunction and gastrointestinal disorders (e.g. IBD). On the other hand, a depressed or reduced level of p11 in a subject compared to that in a control subject constitutes a positive diagnosis of disorders associated with low levels of p11, e.g. depression, obsessive compulsive disorders, drug addiction, eating disorders, attention deficit disorder or attention deficit hyperactive disorder. In a preferred embodiment, the invention encompasses a method of diagnosing in a subject suffering from depression, comprising assaying p11 level in said subject and comparing such level to the p11 level in a control subject, wherein a depressed level of p11 in said subject compared to that in a control subject constitutes a positive diagnosis of depression.

As used herein, the term "antibody" refers to intact molecules as well as fragments thereof, such as Fa, F(ab')$_2$, and Fv, which are capable of binding the epitopic determinant. Antibodies that bind p11 polypeptides can be prepared using intact polypeptides or fragments containing small peptides of interest as the immunizing antigen. The polypeptides or peptides used to immunize an animal can be derived from the translation of RNA or synthesized chemically, and can be conjugated to a carrier protein, if desired. Commonly used carriers that are chemically coupled to peptides include bovine serum albumin and thyroglobulin. The coupled peptide is then used to immunize an animal (e.g., a mouse, a rat or a rabbit).

Factors for consideration for optimizing a therapy for a patient include the particular condition being treated, the particular mammal being treated, the clinical condition of the individual patient, the site of delivery of the active compound, the particular type of the active compound, the method of administration, the scheduling of administration, and other factors known to medical practitioners. The therapeutically effective amount of an active compound to be administered will be governed by such considerations, and is the minimum amount necessary for the treatment of p11 mediated disorders, preferably, depression.

Suitable antibodies to p11 or related regulatory proteins can be obtained from a commercial source or produced according to conventional methods. For example, described herein are methods for the production of antibodies capable of specifically recognizing one or more differentially expressed gene epitopes. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

For the production of antibodies to p11 polypeptides discussed herein, various host animals may be immunized by injection with the polypeptides, or a portion thereof. Such host animals may include, but are not limited to, rabbits, mice, and rats. Various adjuvants may be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as target gene product, or an antigenic functional derivative thereof. For the production of polyclonal antibodies, host animals such as those described above, may be immunized by injection with the polypeptides, or a portion thereof, supplemented with adjuvants as also described above.

Monoclonal antibodies, which are homogeneous populations of antibodies to a particular antigen, may be obtained by any technique which provides for the production of antibody molecules by continuous cell lines in culture, such techniques being well known in the art. Such antibodies may be of any immunoglobulin class including IgG, IgM, IgE, IgA, IgD and any subclass thereof, preferably IgG. The hybridoma or transformed cell line producing the mAb of this invention may be cultivated in vitro or in vivo. Alternatively, techniques described for the production of single chain antibodies can be adapted to produce differentially expressed gene-single chain antibodies. Single chain antibodies are formed by linking the heavy and light chain fragments of the Fv region via an amino acid bridge, resulting in a single chain polypeptide.

Detection of the antibodies described herein may be achieved using standard ELISA, FACS analysis, and standard imaging techniques used in vitro or in vivo. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I $^{35}$S or $^{3}$H.

For example, in a typical forward assay, unlabeled antibody is immobilized on a solid substrate and the sample to be tested brought into contact with the bound molecule. After a suitable period of incubation, for a period of time sufficient to allow formation of an antibody-antigen binary complex, a second antibody, labeled with a reporter molecule capable of inducing a detectable signal, is added and incubated, allowing time sufficient for the formation of a ternary complex of antibody-antigen-labeled antibody. Any un-reacted material is then washed away, and the presence of the antigen is determined by observation of a signal, or may be quantified by comparing with a control sample containing known amounts of antigen. Variations on the forward assay include the simultaneous assay, in which both sample and antibody are added simultaneously to the bound antibody, or a reverse assay in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique. For the immunoassays of the present invention, the only limiting factor is that the labeled antibody be an antibody which is specific for the p11 polypeptide or related regulatory protein, or fragments thereof.

The most commonly used reporter molecules are either enzymes, fluorophore- or radionuclide-containing molecules. In the case of an enzyme immunoassay an enzyme is conjugated to the second antibody, usually by means of glutaraldehyde or periodate. As will be readily recognized, however, a wide variety of different ligation techniques exist, which are well-known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. A solution containing the appropriate substrate is then added to the tertiary complex. The substrate reacts with the enzyme linked to the second antibody, giving a qualitative visual signal, which may be further quantitated, usually spectrophotometrically, to give an evaluation of the amount of polypeptide or polypeptide fragment of interest which is present in the serum sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

When the antibodies are intended for therapeutic use, it is preferred that they have a human constant region so as to minimize their immunogenicity. Chimeric antibodies are made by splicing DNA encoding the variable region from a donor antibody molecule of appropriate antigen specificity together with DNA encoding the constant region of a human antibody molecule. The antibodies may be further modified to provide humanized antibodies, which are additionally modified to remove nonhuman residues. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. The humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Alternatively, antibodies derived from nonhuman sources but using fully human immunoglobulin genes may be made e.g., using phage display techniques or transgenic animals, e.g., transgenic mice having human IgV and IgC genes, and such antibodies should exhibit minimal immunogenicity.

A "therapeutically effective amount" as used herein refers to an amount of drug sufficient to treat or ameliorate the pathological effects of p11/5-HT receptor related disorders. For instance, a therapeutically effective amount of p11 modulator sufficient to treat or ameliorate the pathological effects of a p11/5-HT receptor related disorder is an amount sufficient to either induce or inhibit p11 expression or regulate (either up or down) $5\text{-HT}_{1B}$ receptors levels at the neuronal plasma membrane. Therefore, a therapeutically effective amount of p11 modulator sufficient to treat or ameliorate the pathological effects of depression is an amount sufficient to either induce p11 expression or increase p11's ability to recruit $5\text{-HT}_{1B}$ receptors to the neuronal plasma membrane. Conversely, a therapeutically effective amount of p11 modulator sufficient to treat or ameliorate the pathological effects of anxiety disorders would be an amount sufficient to either inhibit p11 expression or down-regulate $5\text{-HT}_{1B}$ receptors at the neuronal plasma membrane. p11 modulator may be administered via known methods in the art including intravenous, subcutaneous, intramuscular, transdermal or intracerebral administration. Administration may be rapid as by injection or over a period of time as by slow infusion or administration of a slow release formulation.

The phrase "p11 knock-out" refers to a DNA sequence that has a total or partial defect, alteration or mutation or is devoid or deficient in the p11 gene. A "p11 knock-out mouse" or "p11 knock-out transgenic mouse" therefore refers to a mouse wherein the DNA introduced into said mouse contains a defect, deficiency, mutation or alteration in the gene that expresses p11 proteins. As a result of the defect or deficiency in p11 gene, a p11 knock-out mouse has fewer $5\text{-HT}_{1B}$ receptors at the neuronal plasma membrane and/or exhibits reduced or no $5\text{-HT}_{1B}$ receptors at the neuronal plasma membrane, thereby exhibiting a depression-like phenotype compared to wild-type mouse. The terms "knock-out" may refer to a deviation anywhere from 1 nucleotide to deletion of the entire gene compared to the original gene. Knock-out mice may be generated by using any known techniques in the art such as targeted homologous recombination.

The term "recombinant" refers to DNA which has been isolated from its native or endogenous source and modified either chemically or enzymatically to delete naturally-occurring flanking nucleotides or provide flanking nucleotides that do not naturally occur. Flanking nucleotides are those nucleotides which are either upstream or downstream from the described sequence or sub-sequence of nucleotides.

As used herein, a "vector" is something which delivers a recombinant nucleic acid to a desired cell or tissue, for example a virus which can infect, transfect, or transiently or permanently transduce a cell. It is recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). For purposes of this application, a vector may also be a cell comprising the recombinant nucleic acid. It is recognized that vectors typically include an expression cassette placing the nucleic acid of interest under the control of a promoter, or may simply include a promoter flanked by targeting sequences to achieve insertion upstream of the gene whose expression is desired. Vectors include, but are not limited to replicons (e.g., plasmids, bacteriophages) to which fragments of DNA may be attached and become replicated. Vectors thus include, but are not limited to RNA, autonomous self-replicating circular DNA (plasmids), and include both the expression and non-expression plasmids. Where a recombinant microorganism or cell culture is described as hosting an "expression vector" this includes both extrachromosomal circular DNA and DNA that has been incorporated into the host chromosome(s). Where a vector is being maintained by a host cell, the vector may either be stably replicated by the cells during mitosis as an autonomous structure, or may be incorporated within the host's genome.

The phrase "nucleic acid sequence encoding" refers to a nucleic acid containing codons which, when transcribed and/or translated, express a specific protein or peptide. The nucleic acid sequence may additionally comprise flanking sequences, introns, and/or sequences encoding peptides which are subsequently cleaved post-translation. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It being further understood that the sequence includes the native sequence as well as sequences utilizing degenerate codons, e.g., to adapt the sequence to the codon preference in a specific host cell.

"Nucleic acids", as used herein, may be DNA or RNA. Nucleic acids may also include modified nucleotides that permit correct read through by a polymerase and do not alter expression of a polypeptide encoded by that nucleic acid.

EXAMPLES

Example 1

Yeast Two-Hybrid Screen

To better understand the function of $5\text{-HT}_{1B}$ receptors, the third intracellular loop of this receptor is used as bait in a yeast two-hybrid screen. The third intracellular loop of the rat 5-HT1B receptor (amino acids 226-311) is PCR amplified from a the full-length cDNA rat brain library and subcloned into the Nco I/Sal sites of a bait pAS2-derived vector, for expression as a GAL4 DNA-binding domain fusion protein. The $5\text{-HT}_{1B}$ receptor-bait plasmid is transformed, by using the lithium acetate method, into yeast strain CG1945. The size and expression level of the fusion protein are checked by immunoblot by using an anti-GAL4 DNA binding domain antibody. The pACT2 rat brain cDNA library is transformed into yeast strain Y187. Bait and prey transformants are mated on YPD medium and plated on medium (–LWH) selective for the expression of the histidine reporter gene. 244×106 diploid clones from the pACT2 rat brain cDNA library are screened. After growth on this medium, a 5-bromo-4-chloro-3-indolyl-D-galactoside overlay assay is performed. More than 300 clones grow on selective medium and are positive for the β-galactosidase reporter gene. Yeast extracts are prepared from double positive clones. Prey inserts are amplified by PCR ((SEQ ID NO: 1) 5'-CGCGTTTGGAATCACTACA GGGATG-3' and (SEQ ID NO: 2) 5'-GAAATTGAGATGGT-GCACGATGCAC-3') and sequenced using a prey vector oligonucleotide ((SEQ ID NO: 3) 5"-GGCTTACCCATACGAT-GTTC-3'). p11 is identified as the major prey by a BLAST search. p11 prey plasmid clones are selectively rescued from the yeast, transformed into *Escherichia coli* for DNA amplification and retransformed into the yeast strain Y187 with (i) the original 5-HT$_{1B}$ receptor-bait vector, (ii) the bait control vector to test for transactivation, (iii) two other irrelevant bait constructs, pRP21 and CΔ115, or (iv) bait constructs corresponding to the third intracellular loops of 5-HT1A, 5-HT2A, 5-HT5A, 5-HT6, D1 or D2 receptors, to test the specificity of the interaction. The baits corresponding to 5-HT$_{1A}$ (amino acids 218-345), 5-HT$_{2A}$ (amino acids 236-302), 5-HT$_{5A}$ (amino acids 233-295), 5-HT$_6$ (amino acids 209-265), D1 (amino acids 256-312) and D2 (amino acids 211-343) receptors, respectively, are made by PCR-amplification from the rat brain cDNA library and subcloning into the pAS2-derived vector. Each of these baits is co-transformed into yeast with the p11 prey construct and the interaction analyzed by using –LW or –LWH medium and an X-gal overlay assay. All the co-transformants grew on the non-selective medium (–LW) control plates. On the selective medium (–LWH), a positive interaction of p11 with 5-HT1B receptors, but not with any of the other baits, is detected.

Twenty-six out of 29 double positive prey clones encode the gene for p11. p11 interacts with 5-HT$_{1B}$ receptors in this assay but not with 5-HT$_{1A}$, 5-HT$_{2A}$, 5-HT$_{5A}$, 5-HT$_6$, dopamine D$_1$ or dopamine D$_2$ receptors, two irrelevant baits (Cdelta115 and pRP21), or the empty plasmid, showing the specificity of p11's association with 5-HT$_{1B}$ receptor.

Example 2

Co-Immunoprecipitation

HeLa cells, which contain endogenous p11 (S1), are grown in DMEM medium to 60% confluence and transfected with pcDNA3.1-5-HT1BR-V5 or empty plasmid constructs with Lipofectamine according to the manufacturer's protocol. After transfection, cell extracts are solubilized at 4° C. (in 50 mM Tris, pH 7.4/150 mM NaCl/2 mM EDTA/2 mM EGTA/ 0.1% Triton and protease inhibitors). Cell extracts are immunoprecipitated with anti-V5 monoclonal antibody, incubated with protein G and thoroughly washed. In other experiments, brain tissue from cerebral cortex of wild-type and p11 KO mice is homogenized in solubilization buffer at 4° C. Brain extracts are immunoprecipitated with a polyclonal 5-HT$_{1B}$ receptor antibody, incubated with protein A and thoroughly washed. The immunoprecipitates froth the cells and the brain tissue are run out on an SDS-PAGE gel and transferred onto PVDF membranes. Immunoblotting is carried out using a mouse monoclonal antibody against p11 (1/100). Antibody binding is detected by incubation with a secondary HRP-linked antibody directed towards mouse IgG and enhanced chemiluminescence.

p11 coimmunoprecipitates with 5-HT$_{1B}$ receptors in HeLa cells and brain tissue.

Example 3

Immunofluorescence

HeLa cells are transfected with pcDNA3.1-5-HT1BR or pcDNA3.1-V5 constructs. Thirty six hours posttransfection cells are fixed with 4% paraformaldehyde/0.01 M PBS for 10 min. Non-specific staining is blocked by incubation with 10% BSA in PBS. 5-HT$_{1B}$ receptors and p11 are visualized by incubation with anti-V5-FITC antibody (1/500) and antimouse p11 antibody (1/1000) followed by Alexa Fluor 568-labeled goat anti-mouse secondary antibodies (1/500). After washing in PBS, cover slips are mounted on slides by using Gel/Mount. Images of fluorescent proteins are acquired using a laser-scanning microscope.

Immunofluorescence shows a prominent colocalization between p11 and 5-HT$_{1B}$ receptors at the cell surface.

Example 4

In Situ Hybridization Experiments

All animal experiments are performed according to guidelines from institutional animal care committees at the Rockefeller University, the Karolinska Institute and the National Institutes of Health. Brains from adult male Sprague Dawley rats are used to determine the regional distribution of p11 gene expression and its co-distribution with 5-HT1B receptor gene expression. For some experiments, brains from p11 KO mice and their wild-type counterparts are used. To study the effects of psychoactive drug treatment on p11 mRNA expression, wild-type adult male C57B16 mice are treated with a single injection or repeated injections (once daily for 14 days) of, vehicle, imipramine (10 mg/kg, i.p.), haloperidol (1 mg/kg, i.p.), diazepam (5 mg/kg, i.p), tranylcypromine (10 mg/kg, i.p.) or risperidone (1 mg/kg, i.p.). Animals are killed 1 hour after the last injection. To study the effect of electroconvulsive treatment (ECT) on p11 expression, male Sprague Dawley rats (200 gram) are exposed to daily ECT via ear clip electrodes (45 mA; 0.3 sec) for 10 days and killed 18 hours after the last stimulation. Control animals received sham treatment in which electrodes are clipped onto the rat ears but no current is applied.

There is an upregulation of p11 mRNA in the forebrain following the 14 day treatment with imipramine and with tranylcypromine, and following the repeated electroconvulsive therapy, but not with haloperidol, risperidone, or diazepam.

Example 5 p11 Protein Levels in Mouse Depression Model and in Normal and Depressed Humans

Wild-type adult male C57B16 mice are treated once daily for 14 days with vehicle or imipramine (10 mg/kg, i.p.) and killed 1 hour after the last injection. Male Sprague Dawley rats are exposed to daily ECT via ear clip electrodes (45 mA; 0.3 sec) for 10 days and killed 18 hours after the last stimulation. Adult female helpless H/Rouen mice and non-helpless NH/Rouen mice are sacrificed. From these 3 different treatment groups and their corresponding controls, frontal cortices are dissected out and frozen.

Fresh-frozen tissue from the human cingulate cortex of normal controls and patients who suffered from major depression is obtained from the Stanley Foundation Neuropathology Consortium. The frozen cortices are sonicated in 1% SDS and boiled for 10 min. Small aliquots of the homogenate are retained for protein determination by the bicinchoninic acid protein assay method.

Equal amounts of protein are processed by using 10-20% gradient acrylamide gels. Immunoblotting is carried out with either polyclonal or monoclonal antibodies against p11 (1/1000 for the human samples and 1/200 for the rodent samples) and polyclonal antisera against actin (1/1000). Antibody binding is detected by enhanced chemiluminescence and quantified by densitometry, using National Institutes of Health IMAGE 1.63 software. The level of p11 is normalized to the level of actin. All data are presented as normalized levels.

To study the regulation of p11 mRNA in a genetic mouse model of depression, forebrain tissue from adult female and male helpless H/Rouen mice and from non-helpless NH/Rouen mice are compared. p11 mRNA and protein are markedly lower in H/Rouen mice. Similar results are found with the two genders.

Forty-µm-thick cryostat-cut sections of human cingulated cortex of normal controls and patients who suffered from major depression are obtained from the Stanley Foundation Neuropathology Consortium. The analyzed samples are from both genders (6 females and 9 males in both the normal and depression groups) and aged 29-68 (normal) and 30-65 (depression) years. The duration of the disease among the depressed patients varies from 1 to 42 years. Seven of the depressed individuals died by suicide. The post-mortem intervals of the brain tissue before it is frozen are 8-42 (normal) and 7-47 (depression) hours and the pH of the tissue 5.8-6.6 (normal) and 5.9-6.5 (depression). In situ hybridization probes are made by PCR amplification of nucleotides 1159-1420 of the coding sequence of the rat 5-HT1B receptor gene, nucleotides 1-293 of the coding sequence of the mouse or human p11 genes and nucleotides 1-287 of the coding sequence of the rat p11 gene, respectively. The different PCR fragments are subcloned into the pCRII-TOPO vector. With the exception of the studies on human tissue, 12-µm-thick cryostat sections are made for all studies. Sections are hybridized with [$□^{-35}S$]UTP-labeled riboprobe repared by in vitro transcription from cDNA corresponding to the rat 5-HT1B receptor gene or mouse, rat or human p11 gene as previously described (S5). After hybridization, the sections are exposed to Biomax MR film for 7 to 24 days and analyzed using the NIH Image 1.63 software. Unless indicated, analyses are made in the prelimbic/anterior cingulate cortex. Some sections are dipped into Ilford K5 emulsion for cellular analysis. After 8 weeks, the sections are developed, Nissl-stained and mounted.

Similar to the H/Rouen mice, p11 mRNA and protein are down-regulated in the anterior cingulate cortex in patients who had suffered from unipolar major depression disorder.

Example 6 p11/5-HT$_{1B}$ Receptor Co-Transfection Experiment

COS 7 cells, which contain low, if any, native p11, are transfected with p11 (pcDNA3.1-p11), with 5-HT$_{1B}$ (pcDNA3.1-5-HT1BR-V5), with dopamine D$_1$ receptors (pcDNA3.1-D1R-V5), or empty plasmid. Plated COS 7 cells are incubated with medium containing 1 mg/ml Sulfo-NHS-LC-Biotin for 30 min on ice. Cells are rinsed in TBS to quench the biotin reaction. Cells are lysed in 300 µl of modified RIPA buffer (1% Triton X-100, 0.1% SDS, 0.5% deoxycholic acid, 50 mM NaPO4, 150 mM NaCl, 2 mM EDTA, 50 mM NaF, 10 mM sodium pyrophosphate, 1 mM sodium orthovanadate, 1 mM PMSF, and 1 mg/ml leupeptin). The homogenates are centrifuged at 14,000 g for 15 min at 4° C. Fifteen µl of the supernatant are removed to measure total levels of 5-HT$_{1B}$ receptors. The remaining supernatant is incubated with 100 µl of 50% Neutravidin agarose for 3 hrs at 4° C. and briefly centrifuged. The supernatant, containing cytosolic 5-HT$_{1B}$ receptors, is collected. Thereafter the agarose beads are washed 3 times with RIPA buffer and, after the final brief centrifugation, bound proteins are resuspended in 40 µl of SDS sample buffer and boiled. Quantitative western blots are performed on total, cytosolic and biotinylated (surface) proteins using anti-V5 (to detect 5-HT$_{1B}$ receptors; 1:1000) and anti-p11 (1:1000) antibodies. Immunoreactive bands are detected by enhanced chemiluminescence followed by autoradiography. The intensity of the bands is quantitated using NIH Image 1.63 software. The surface/total ratio is calculated for each well. Control experiments confirmed that the intracellular protein actin is not biotinylated in this assay.

Cells co-transfected with 5-HT$_{1B}$ receptors and p11 exhibit more 5-HT$_{1B}$ at the cell surface than cells transfected with 5-HT$_{1B}$ receptors alone. In contrast, the ratio of surface-to-total dopamine D$_1$ receptors is similar in the presence of absence of p11.

Example 7

CAMP Measurements in COS 7 Cells

COS 7 cells grown in DMEM medium are transfected with 5-HT1B receptors and/or p11. Thirty six hours later the cells are pretreated with theophylline (5 mM) and pargyline (10 µM) for 15 min. Vehicle or forskolin (10 µM) with or without serotonin (10 µM), is then added for another 15 minutes. At the end of the treatment, the drug-containing medium is removed, the wells rinsed in PBS and the cells harvested. cAMP formation is quantitated by a direct cAMP enzyme immunoassay kit according to the manufacturers instructions. Control experiments show that serotonin does not alter cAMP formation in untransfected COS 7 cells.

The ability of serotonin (10 mM) to counteract forskolin-induced cAMP formation in COS-7 cells transfected with the 5-HT$_{1B}$ receptor is increased in the presence of cotransfected p11. There is no significant difference in the cAMP responses to forskolin with or without p11. Data are normalized to forskolin-stimulated conditions, with or without p11, and represent means T SEM.

Example 8

Generation and Analysis of Transgenic Mice Overexpressing p11

Transgenic mice with doxycycline-regulatable overexpression of p11 under the calcium/calmodulin-dependent protein kinase II (CamKII) promoter are generated. Mouse p11 is fused with a Myc epitope tag using PCR and subcloned into the Sal I/Hind III sites of pTet-splice (S6). This plasmid (pTetOp-p11-Myc) is transfected into tTA-expressing CHO cells (kind gift from Dr Patrick Allen). The expression of Myc from extracts of these cells is confirmed by immunoblotting using an anti-Myc (1:1000) antibody. After the confirmation that the p11-Myc is expressed, a DNA fragment (containing pTetOp-p11-Myc, SV40 intron, and poly(A)+signal) is linearized, purified by electroelution \and microinjected into the pronuclei of oocytes from C57BL6 mice and implanted in pseudopregnant C57BL6/CBA mice (Rockefeller University Transgenic Facility). Tail DNA is analyzed for the transgene by PCR ((SEQ ID NO: 4) 5'-TATAGTCGACATGATGC-CATCCC AAATGG-3' and (SEQ ID NO: 5) 5'-TATAAAGCTTCTAC AAATCTTCTTCAGAAAT-CAATTTT TGTTCAGATTTCTTCCCCTTCTG-3'). Founder mice positive for the pTetOp-p11-Myc construct are crossbred with C57B16 mice to generate F1 mice. F2 homozygous pTetOp-p11-Myc-transgenic mice are obtained by crossbreeding F1 siblings. (The homozygous genotype is confirmed by crossbreeding them with wild-type mice.) These mice are crossbred with C57B16 mice expressing tTA under the CamKII promoter (S7). The mice are genotyped by PCR with the abovementioned primers (to detect p11-Myc) and (SEQ ID NO: 6) 5'-GAGCTGCTTAATGAGGTCG GAATC-3' and (SEQ ID NO: 7 5'-TCTAAAGGGCAAAAGTGAGTATGG-3' (to detect tTA). The overexpression of p11-Myc in double transgenic mice is confirmed by immunoblotting using an anti-Myc antibody and by in situ hybridization against the mouse p11 gene (FIG. S2). The expression of CamKII-driven tTA is detected using in situ hybridization with a riboprobe against the coding region of tTA (kind gift from Dr Alexei Morozov, Columbia University) (FIG. S2). In the behavioral experiments, double transgenic mice are compared with littermates expressing none or one the transgenes serving as control mice. Some double transgenic mice receive doxycycline 50 mg/l in their drinking water for 18 days before the experiment.

In the absence of doxycycline, transgenic mice have elevated p11 in neurons that do not contain serotonin in the forebrain, but not in serotonin neurons in the raphe nuclei. These mice have increased functional $5\text{-}HT_{1B}$ receptors in substantia nigra, and exhibit reduced thigmotaxis (an index of anxiety-related distress) and increased horizontal activity in the open-field test. They also show a decreased immobility in the tail suspension test (an index of depression-like state). Thus, mice overexpressing p11 act as if they were treated with antidepressants, although a confounding factor is that they appear to be generally hyperactive. Transgenic mice treated with doxycycline have normalized p11 expression (FIG. S4) and no significant alterations of thigmotaxis, immobility, or horizontal activities.

Example 9

Generation and Analysis of p11 Knock-Out Mice

Generation and Analysis of p11 KO Mice.

Using a probe from the coding sequence of rat p11, 6 genomic clones are isolated from a BAC library screen. A 13.7-kb Bam HI fragment is subcloned from a BAC Clone and mapped by restriction enzyme analysis. The mouse p11 gene contains an ATG-containing exon, a 3.5-kb intron, followed by another exon with the stop codon. A 11.3 kb targeting vector (5' Hinc II-Bgl II+[Bam HI-loxPNeoloxP-Kpn I]+Apa I*-Eco RV 3') spanning the ATG-containing exon of the p11 gene is made in pBSK(−) (FIG. S5). The targeting vector is electroporated into 129SvEv ES cells and selected for recombinant clones by G418. ES clones are identified as positive for homologous recombination by southern blotting using 5' and 3' external probes (300-bp Bam HI/Bsp M1 fragment and 285-bp Bam HI/Sca I fragment, respectively) in an analysis of ES cell DNA digested with Spe I and Bam HI/Sal I, respectively. Positive clones are injected into C57BL/6 blastocysts, and chimeric males are bred with C57BL/6 females to obtain germ-line transmission. Heterozygous offspring are mated to generate knockout and wild-type mice. Southern blotting from tail DNA confirmed that both alleles are mutated in p11 KO mice (FIG. S5). The absence of the p11 gene in the p11 knockout mice is further confirmed using in situ hybridization with a probe against the mouse p11 gene (FIG. S5). A PCR procedure, using the following oligonucleotides, (SEQ ID NO: 8) 5'-CATTCA-GAGGTGAACCCTGCTGAGGG-3', (SEQ ID NO: 9 5'-CCTGTCAGCCACTCTATAT GCTCCTAATC-3' and (SEQ ID NO: 14 5'-GGCCAGCTCATTCCTCCC ACTCATG-3', is developed to distinguish wild-type, heterozygote and knock-out mice (FIG. S5). This PCR-based approach is used for routine genotyping. Except for studies with primary cortical cultures, all experiments are performed on p11 KO and wild-type littermates generated from heterozygote breeding. The heterozygote×heterozygote breeding yielded 29% wild-type, 53% p11 heterozygote and 18% p11 KO mice. It is unclear why there are fewer KO mice, but p11 has been found to be involved in early embryonic implantation (S8). Heterozygote p11 mice are backcrossed for two generations with C57B16 mice. Microsatellite genotyping, using 104 specific C57B16 markers (Rockefeller University Genomics Resource Center), shows that heterozygote p11 mice used for breeding of experimental animals are on a 74±2.8% C57B16 background.

Quantitative Receptor Autoradiography.

Cryostat sections (12 µm thick) are made from p11 KO and wild-type mice. $5\text{-}HT_{1B}$ receptors are detected by incubating the sections in 170 mM Tris/150 mM NaCl pH 7.4 (25° C.) containing the antagonist [$^{125}$I]cyanopindolol (0.3, 1, 3, 10, 30, 100 pM; 2200 Ci/mmol), 100 nM 8-OH-DPAT as a $5\text{-}HT_{1A}$ blocker, and 30 µM isoproterenol, as β-adrenergic receptor blocker, for two hours (S9). Non-specific binding is determined by measurements in the presence of 100 µM serotonin. In displacement experiments, increasing concentrations of serotonin (0, 0.3, 1, 3, 10, 30, 100, 300, 1000, 10000 nM) are incubated with 10 pM [$^{125}$I]cyanopindolol as described above. $5\text{-}HT_{1B}$ receptors are also detected by incubating the sections in 9 170 mM Tris/4 mM CaCl2/0.1% ascorbic acid pH 7.4 (25° C.) with the antagonist [$^{3}$H]GR125743 (0.3, 1, 3, 10, 30 nM; 80 Ci/mmol; GE Healthcare) for two hours. Nonspecific binding is determined by measurements in the presence of 100 µM serotonin. $5\text{-}HT_{1A}$ receptors are detected by incubating the sections in 50 mM Tris pH 7.4, 4 mM CaCl$_2$, 1 mM MgCl$_2$ and 0.1% bovine serum albumin (25° C.) with agonist [$^{3}$H]8-hydroxy-2-(di-n-propylamino)-tetralin ([$^{3}$H]8-OH-DPAT; 10 nM; 125 Ci/mmol; GE Healthcare), 300 nM SB-269970, as a 5-HT7 receptor blocker, for one hour. Non-specific binding is determined by measurements in the presence of 100 µM serotonin. D1-like receptors are detected by incubating the sections in 25 mM Tris/100 mM NaCl/1 mM MgCl$_2$/1 µM pargyline/20 nM mianserin/ 0.001% ascorbic acid containing the antagonist [$^{3}$H]7-chloro-2,3,4,5-tetrahydro-3-methyl-5-phenyl-1H-3-benza-zepine-7-ol ([$^{3}$H]SCH 23390; 2 nM; 87.0 Ci/mmol) for 2 hours. Non-specific binding is determined by measurements in the presence of 100 µM SKF82958. D2-like receptors are detected by incubating the sections with 170 mM Tris/120 mM NaCl/5 mM KCl/2 mM CaCl$_2$,/1 mM MgCl$_2$,/10 µM GTP/0.001% ascorbic acid containing the antagonist [$^{3}$H]raclopride (5 nM; 72 Ci/mmol) for one hour. Non-specific binding is determined by measurements in the presence of 100 µM quinpirole. At the end of all autoradiographic experiments, sections are rinsed 2×5 min in their corresponding cold binding buffers, dipped in distilled water at 4° C. and dried under cold air. The sections are apposed to Biomax MR films for 3-5 days ([$^{125}$I]cyanopindolol) or 4-10 weeks ([$^{3}$H]GR125743, [$^{3}$H]8-OHDPAT, $^{3}$H]SCH23390, [$^{3}$H]raclopride) together with [$^{125}$I] or [$^{3}$H] microscales. Optical density measurements are obtained in several brain regions with the NIH Image 1.63 image analysis system. Specific binding is calculated by digital subtraction of nonspecific labeling from total binding. Standard curves generated from [$^{3}$H] or [$^{125}$I] microscales are used to convert optical densities into femtomoles per milligram of protein. Data obtained from saturation and displacement experiments are analyzed using non-linear regression equations.

Autoradiographic ligand-binding experiments showed that there are fewer binding sites for the $5\text{-}HT_{1B}$ receptor antagonist radioligands [$^{125}$I]iodocyanopindolol and [$^{3}$H]GR125743 in globus pallidus in p11 KO than in wild-type mice. Similarly, [$^{125}$I]iodocyanopindolol binding is lower in substantia nigra pars reticulata in p11 KO than in wild-type mice (77.3±5.8 versus 98.8±6.2 fmol/mg protein; P<0.05 Student's t test). There is no difference in the affinity of serotonin to displace bound [$^{125}$I]iodocyanopindolol between wild-type and p11 KO mice [median effective concentration ($EC_{50}$) values: 57 versus 52 nM]. No differences in the amounts of 5-$HT_{1A}$, $D_1$, or $D_2$ receptors are detected between the wild-type and p11 KO mice. [$^{125}$I]Iodocyanopindolol binding is also reduced in H/Rouen mice versus NH/Rouen mice.

[$^{35}$S]GTPγS Binding in Response to 5-HT1A or 5-HT1B Receptor Stimulation.

Fresh cryostat sections (12 μm) from wild-type, p11 KO and p11 transgenic mice are preincubated for 30 min in Tris-HCl 50 mM (pH 7.4) supplemented with 100 mM NaCl, \10 3 mM MgCl2, 0.2 mM EGTA, 2 mM GDP and 1 U/ml adenosine deaminase to remove endogenous adenosine. The sections are thereafter incubated for two hours at 25° C. in the same solution containing 40 pM [$^{35}$S]GTP S, with (stimulation condition) or without (basal condition) 50 μM of the 5-HT1A receptor agonist, 8-OH-DPAT, or the 5-HT1B receptor agonist, anpirtoline. Non-specific labeling (background) is determined on autoradiographs from adjacent sections incubated with 10 μM of unlabeled GTP S. Sections are rinsed twice (3 min each) in 50 mM Tris-HCl buffer, once (30 sec) in distilled water to remove the buffer salts, and air-dried. The autoradiographs are obtained by 2-4 days exposure on Biomax MR film. Optical density measurements are obtained in several brain regions with the NIH Image 1.63 image analysis system.

The reduced number of 5-$HT_{1B}$ receptors at the cell membrane in p11 KO mice is reflected in a reduced ability of the 5-$HT_{1B}$ receptor agonist anpirtoline to increase [$^{35}$S]guanosine 5'-O-(3'-thiotriphosphate (GTP-S) binding in globus pallidus in these mice. In contrast, there is no difference in [$^{35}$S]GTP-S binding by 8-OH-DPAT [(+/−)-8-hydroxy-2-(di-n-propylamino)tetralin], a 5-$HT_{1A}$ receptor agonist, in wild-type and p11 KO mice (6.0±2.1 versus 5.0±2.0 optical density units). The decreased number of functional 5-$HT_{1B}$ receptors at the cell surface of p11 KO mice is also reflected in a loss of ability of serotonin and of anpirtoline to down-regulate phospho-Thr$^{202}$/Tyr$^{204}$-ERK1/2 (extracellular signal-regulated kinase) levels in primary cortical cultures from p11 KO mice and of anpirtoline to decrease phospho-Ser$^9$-synapsin I, a site phosphorylated by cAMP-dependent protein kinase, in striatal slices from p11 KO mice.

Western Blotting to Detect Phosphorylated ERK1/2 in Primary Cortical Cultures.

Cortices are removed from E18 mice generated from WT×WT or p11KO×p11KO breedings, trypsinized (0.25%), dissociated by trituration and plated onto poly-L-lysine (1 mg/ml) coated six-well plates. The cultures (500,000 cells/ml) are grown in medium containing DMEM with 5% fetal bovine serum, 4 mM L-glutamine, B-27 nutrient supplement, penicillin (5 U/ml), and streptomycin (5 μg/ml). After two weeks, the cultures are treated with vehicle, serotonin (10 μM) or anpirtoline (10 μM) for 15 minutes. At the end of the treatment, the drug-containing medium is removed, the wells rinsed in ice-cold PBS, the neurons removed by a cell scraper and frozen in liquid nitrogen. Frozen cell samples are sonicated in 1% SDS and boiled for 10 min. Small aliquots of the homogenate are retained for protein determination by the bicinchoninic acid protein assay method. Equal amounts of protein are processed by using 10% acrylamide gels, as described (S10). Immunoblotting is carried out with a phosphorylation-state-specific antibody against phospho-Thr202/Tyr204-ERK1/2 or an antibody that is not phosphorylation-state-specific against total ERK1/2. Antibody binding is detected by enhanced chemiluminescence and quantified by densitometry, using National Institutes of Health IMAGE 1.63 software. The level of the phosphorylated form of ERK1/2 is normalized to its total level. All data are presented as normalized levels.

Western Blotting to Detect Phosphorylated Synapsin I in Brain Slices.

Slices (300 μm) from the striatum are prepared from wild-type and p11 KO mice as described (S10). The slices are preincubated in Krebs buffer (118 mM NaCl/4.7 mM KCl/1.5 mM Mg2SO4/1.2 mM KH2PO4/25 mM NaHCO3/11.7 mM glucose/1.3 mM CaCl2) at 30° C. under constant oxygenation (95% O2/5% CO2) for 60 min, with a change of buffer after 30 mM. Slices are treated with vehicle or anpirtoline (50 μM) for 2 min. After drug treatment, the buffer is removed, the slices are rapidly frozen on dry ice, sonicated in 1% SDS and boiled for 10 min. Small aliquots of the homogenate are retained for protein determination by the bicinchoninic acid protein assay method. Equal amounts of protein are processed by using 10% acrylamide gels. Immunoblotting is carried out with a phosphorylation-state-specific rabbit polyclonal antibody against phospho-Ser9-synapsin I, a site that is phosphorylated by PKA and CamKII, or a rabbit polyclonal synapsin antibody that is not phosphorylation-state-specific. Antibody binding is detected by enhanced chemiluminescence and quantified by densitometry, using National Institutes of Health IMAGE 1.63 software. The level of the phosphorylated form of synapsin is normalized to its total level. All data are presented as normalized levels.

Electrophysiology.

Male p11 KO and wild-type mice (4-7 weeks old) are decapitated under fluorothane anesthesia. Their brains are rapidly removed and coronal brain slices (400 μm thick), containing the nucleus accumbens, are prepared with a microslicer. Slices are incubated, for at least 1 h, at 32° C. in oxygenated (95% O2+5% CO2) artificial cerebrospinal fluid (aCSF) containing (in mM): 126 NaCl, 2.5 KCl, 1.2 NaH2PO4, 1.3 MgCl2, 2.4 CaCl2, 10 glucose and 26 NaHCO3, pH 7.4. Slices are transferred to a recording chamber mounted on an upright microscope and are continuously perfused with oxygenated aCSF at 28° C. Extracellular field potentials are recorded using a glass micropipette filled with aCSF positioned on the slice surface in the nucleus accumbens. Signals are amplified 500 times via an Axopatch 200B amplifier acquired at 10 kHz, filtered at 2 kHz and recorded on a Computer using acquisition and pClamp9 data analysis software. Synaptic responses are evoked with a concentric bipolar stimulating electrode placed near the recording electrode on the surface of the slice. The dependence of the intensity of the stimulation applied to the slice on the fEPSP amplitude is similar in WT and p11 KO mice, demonstrating that glutamatergic 12 synaptic transmission did not differ between WT and p11 KO mice. Single stimuli (0.1 ms duration) are applied every 15 sec at an intensity yielding 50-70% maximal response as assessed by a stimulus/response curve established for each slice examined by measuring the amplitude of the field potential evoked by increasing stimulus intensities. To evaluate the effect of serotonin receptor activation on glutamatergic synaptic transmission, serotonin is applied in the perfusion solution while measuring fEPSP/PS amplitude. Serotonin (50 μM; in the presence of 10 μM fluoxetine) depresses the amplitude of the fEPSP/PS in slices from WT mice (72 □□2.7% of baseline value) and this effect is abolished in slices from p11 KO mice (98 □□3.6% of baseline value). Numerical values are expressed as means ☐☐SEM. Drugs are applied in the perfusion solution by switching a three-way tap.

Serotonin, via 5-HT$_{1B}$ receptors, reduces glutamate release at terminals of neurons originating from the cerebral cortex and inhibits synaptic transmission at corticostriatal synapses. The amplitude of field excitatory postsynaptic potentials (f EPSPs) evoked by brief electrical stimulation of glutamatergic fibers and recorded extracellularly in the nucleus accumbens is monitored. f EPSPs are mediated by AMPA receptors activated by endogenous glutamate released by electrical stimulation of the slice in both wild-type and p11 KO mice [f EPSP/population spike (PS) reduction 77 and 81%, respectively, compared with baseline, 15 min after the AMPA receptor antagonist 6-cyano-7-nitroquinoxaline-2,3-dione (CNQX)]. When applied in the perfusion solution, serotonin depresses the amplitude of the f EPSP/PS in slices from wild-type mice, but not from p11 KO mice.

Tissue Content of Monoamines and Metabolites.

Male p11 KO, p11 heterozygote and wild-type mice (n=8 per genotype) are sacrificed by focused microwave irradiation and striata, cortices and hippocampi dissected out and frozen on dry ice. The tissue samples are then sonicated in 10 volumes of 0.1N TCA, vortexed and centrifuged at 12,000 g for 2 min. Supernatants are collected and analyzed for serotonin and the serotonin metabolite 5-hydroxyindolacetic acid (5-HIAA) using HPLC coupled with electrochemical detection (HPLC-EC). Serotonin and 5-HIAA are separated with a base deactivated silica-Hypersil 5 μm C18 analytical column (4.6×150 mm) with a mobile phase consisting of 75 mM sodium phosphate monobasic, 350 mg/L 1-octanesulfonic acid sodium salt, 0.5 mM EDTA, 0.8% tetrahydrofuran (HPLC grade, inhibitor-free), and 8% acetonitrile, pH 3 (adjusted with phosphoric acid), at a flow rate of 1.2 ml/min. An electrochemical detector with dual glassy carbon electrodes is used (electrode 1=680 mV, range, 0.5 nA; electrode 2=−100 mV, range, 0.2 nA). Data are collected using EZChrom software that calculated peak heights and sample concentrations. The sensitivity for serotonin and 5-HIAA is 0.1 pmol/ml.

5-HT$_{1B}$ receptors act as autoreceptors and inhibit serotonin release. Because p11 is expressed in the raphe nuclei, the amounts of serotonin and its major metabolite 5-hydroxyindoleacetic acid (5-HIAA) are measured in projection areas, namely, cortex, striatum, and hippocampus in wild-type and p11 KO mice. In accordance with a negative regulation of 5-HT turnover and/or metabolism by 5-HT$_{1B}$ receptors, and a potentiating role of p11 on 5-HT$_{1B}$ receptor function, p11 KO mice have increased levels of serotonin turnover and/or metabolism.

Behavioral Analyses—Open-Field Analysis.

Horizontal activities are measured for 30 minutes (results are analyzed every 5 min period) during daytime in a fully computerized, multicage, red and infrared-sensitive motion detection system. The peripheral activity values are divided 13 by the total horizontal activity values to determine thigmotaxis. In experiments with anpirtoline (5 mg/kg, i.p.) animals are tested 15 min postinjection. Some anpirtolinetreated mice had received daily injections with imipramine (10 mg/kg, i.p.) for 4 weeks until the day before the experiment.

Behavioral Analyses—Tail Suspension Test.

The tail suspension test, a model of antidepressant-like activity, is carried out as described (S11) and is a modified version of that validated for C57B16 (S12) and NMRI mice (S13). Mice are individually suspended by the tail to a horizontal bar (distance from floor is 35 cm) using adhesive tape (distance from tip of tail is 2 cm). Typically, mice demonstrated several escape-oriented behaviors interspersed with temporally increasing bouts of immobility. A 6-min test session is videotaped and scored by an observer who is unaware of the genotype. The parameter recorded is the number of seconds spent immobile. In experiments with anpirtoline (5 mg/kg) and imipramine (10 mg/kg), animals are tested 15 minutes postinjection.

Behavioral Analyses—Sucrose Consumption Test.

A single bottle procedure in individually housed p11 KO mice and wild-type mice is used for testing sucrose consumption. Consumption of a 2% sucrose solution in water is measured during a 96-hour period. In a subsequent experiment, water intake is measured for the same period of time.

To evaluate behavioral effects of p11 deletion, thigmotaxis in wild-type and p11 KO mice is compared under basal conditions and in response to anpirtoline in drug-naïve mice and in mice that have been treated long-term with imipramine. In animals treated with imipramine, anpirtoline causes a significant reduction in thigmotaxis in wild-type mice, but not in p11 KO mice (FIG. 4G). In addition, there is less thigmotaxis in saline-injected wild-type than p11 KO mice (FIG. 4G). Drug-naïve wild-type and p11 KO mice exhibit similar thigmotaxis either in the absence or presence of anpirtoline. There is an increased immobility in the tail suspension test in p11 KO mice compared with wild-type mice, both under baseline conditions and after acute treatment with either anpirtoline or imipramine (FIG. 4H). These behavioral results indicate that p11 KO mice exhibit a depression-like phenotype and that p11 mediates behavioral responses to imipramine via 5-HT$_{1B}$ receptors. In further support of a depression-like phenotype of p11 KO mice, p11 KO mice consume less of a palatable 2% sucrose solution than their wild-type littermates (1.74±0.07 versus 2.17±0.11 ml/g body weight per day; P<0.05 Student's t test), which indicates a decreased responsiveness to sweet reward. Water intake is similar in the p11 KO mice and their wild-type littermates (1.51±0.05 versus 1.42±0.05 ml/g body weight per day), which rules out a role of altered fluid balance in this behavior.

Example 10

Detection of p11 in Human Peripheral Blood Mononuclear Cells (PBMC)

Whole blood (10-15 ml) is collected in a heparinized tube. One ml of blood will yield approximately 1 milj mononuclear cells, although the number varies considerably between individuals. The blood is diluted 1:1 in phosphate-based saline (PBS). 2.5 ml lymphoprep (Medinor cat nr 1114547) is added to 15 ml tubes and 10 ml diluted blood carefully layered on top. The tubes are spun 20 minutes at 1800 rpm and room temperature. Using a Pasteur pipette, PBMC are collected from two tubes into one clean 15 ml tube. This tube is filled with PBS and spun down at 1500 rpm for 10 minutes. The cells are then washed twice in PBS (removes blood platelets as well as lymphoprep). To count, PBMC are diluted in 1 ml of medium (90% fetal calf serum/10% DMSO) per original 10 ml whole blood volume. (Count diluting 1:10 in Trypan Blue). PBMC are frozen at −80° C. (dry ice) or cooler, and stored it and delivered at −80° C. 0.5 milj PBMC per well are added to 96-well plates. The plate is spun and the supernatant discarded. The cells are fixed in BD fixation buffer (BD Biosciences, from kit cat no 554715). The permeabilisation buffer from the same kit is added and the cells are washed. The cells are now ready for intracellular staining. p11 antibody (BD Biosciences; 2.5 ug/ml) is diluted in the permeabilisation buffer and added to the wells. One well is used for IgG1 control. The cells are suspended by pipetting. The cells are incubated for 30 minutes and washed in permeabilization buffer. The secondary antibody (ex goat anti-mouse PE conjugated) is diluted in permeabilization buffer and added to each well. The cells are suspended and incubated for 30 minutes. They are washed twice with permeabilization buffer and once with PBS-1% FCS. For double-staining, the secondary antibody is blocked by washing once with 100 ul PBS-1% FCS-1% NMS (normal mouse serum). The blocking step is necessary to avoid binding of subsequent antibodies to any remaining secondary antibody. To stain surface markers, PBS containing CD14-PerCP (to distinguish monocytes) or CD3-PerCP and CD56-PE (to distinguish T cells and NK cells), or CD19-FITC (to distinguish B cells) is added to each well. The cells are suspended by pipetting and incubated 10 minutes in the refrigerator. They are then washed once with 200ul PBS-1% FCS. Standard FACS procedure is used to determine the staining of p11 in the different types of mononuclear cells. p11 is highly expressed in some white blood cells, monocytes, NK killer cells and CD-8 positive T-cells.

The invention claimed is:

1. A method of diagnosing depression in a subject comprising determining the level of p 11 in a biological sample wherein said biological sample comprises brain tissue or peripheral blood mononuclear cells from said subject and comparing said p 11 level to a reference, wherein a reduced level of p 11 compared to the reference constitutes a positive diagnosis of depression.

2. The method according to claim 1, wherein said peripheral blood mononuclear cells are NK cells and/or CD-8+ T-cells.

3. The method according to claim 1, wherein said peripheral blood mononuclear cells are NK cells.

4. The method according to claim 1, wherein said level of p11 is determined by assaying p11 protein level in the monocytes and/or lymphocytes in said biological sample from said subject.

5. The method according to claim 1, wherein said level of p11 is determined by assaying p11 mRNA level in a biological sample from said subject.

6. The method of claim 1 wherein the level of p11 is determined using a monoclonal antibody specific for p11.

7. The method of claim 6 wherein the detection of said monoclonal antibody is achieved by using standard ELISA, FACS analysis, and/or standard imaging techniques.

8. The method of claim 3 wherein the level of p11 is determined using a monoclonal antibody specific for p11.

9. The method of claim 8 wherein the detection of said monoclonal antibody is achieved using standard ELISA, FACS analysis, and/or standard imaging techniques.

* * * * *

UNITED STATES PATENT AND TRADEMARK OFFICE
CERTIFICATE OF CORRECTION

PATENT NO. : 8,470,548 B2  
APPLICATION NO. : 13/335402  
DATED : June 25, 2013  
INVENTOR(S) : Per Svenningsson et al.

Page 1 of 1

It is certified that error appears in the above-identified patent and that said Letters Patent is hereby corrected as shown below:

On the Title Page, Item (73) please replace the Assignee "INTRA-CELLULAR THERAPIES, INC." that appears on the front page of the patent with "THE ROCKEFELLER UNIVERSITY".

Signed and Sealed this  
Fifteenth Day of July, 2014

Michelle K. Lee  
*Deputy Director of the United States Patent and Trademark Office*